United States Patent
Zou

(10) Patent No.: US 7,684,952 B2
(45) Date of Patent: Mar. 23, 2010

(54) DETERMINING DENSITY CONTRAST AT SUBSURFACE INTERFACE

(75) Inventor: Keshan Zou, Missouri City, TX (US)

(73) Assignee: WesternGeco L.L.C., Houston, TX (US)

( * ) Notice: Subject to any disclaimer, the term of this patent is extended or adjusted under 35 U.S.C. 154(b) by 0 days.

(21) Appl. No.: 11/762,709

(22) Filed: Jun. 13, 2007

(65) Prior Publication Data
US 2008/0312864 A1    Dec. 18, 2008

(51) Int. Cl.
G01N 9/36 (2006.01)
(52) U.S. Cl. .......................... 702/137; 702/14; 702/18; 702/66; 367/14; 367/37
(58) Field of Classification Search ................ 702/189, 702/66, 24, 72, 70, 142, 14, 17, 18; 367/75; 250/559.4; 73/152.05; 340/856.4
See application file for complete search history.

(56) References Cited

U.S. PATENT DOCUMENTS

| | | | | |
|---|---|---|---|---|
| 3,946,356 A | * | 3/1976 | Anstey | 367/68 |
| 4,375,090 A | * | 2/1983 | Thompson et al. | 367/73 |
| 5,001,677 A | * | 3/1991 | Masters | 367/68 |
| 5,583,825 A | * | 12/1996 | Carrazzone et al. | 367/31 |
| 2007/0081422 A1 | * | 4/2007 | Zou et al. | 367/73 |

OTHER PUBLICATIONS

Ostrander, W.J., Plane-wave reflectin coefficients for gas sands at nonnormal angles of incidence, 1984, Geophysics, vol. 49, p. 1637-1648.*

Buland and Omre, "Bayesian linearized AVO inversion," *Geophysics*, 68(1):185-198, 2003.
Hardage et al., "Distinguishing fizz-gas and commercial gas reservoirs with multicomponent seismic technology," Bureau of Economic Geology, The University of Texas, Austin, Texas, Mar. 2006.
Holvik and Amundsen, "Elimination of the overburden response from multicomponent source and receiver seismic data, with source designature and decomposition into PP-, PS-, SP-, and SS- wave responses," *Geophysics*, 70(2):S43-S59, 2005.
Stewart et al., "Converted-wave seismic exploration: applications," *CREWES Research Report*, vol. 12, 2000.
Vant and Brown, "Effects of density and velocity changes on the correlation of P-P and P-S reflection events," *CREWES Research Report*, 14:1-19, 2002.

* cited by examiner

*Primary Examiner*—Hal D Wachsman
*Assistant Examiner*—Mi'schita' Henson

(57) ABSTRACT

Method for subsurface exploration. In one implementation, the method may include receiving a gamma value at a subsurface interface, wherein the gamma value is a ratio of Vp/Vs at the subsurface interface. Vp is the average P wave velocity and Vs is the average S wave velocity. The method may further include receiving a converted wave reflection coefficient at the subsurface interface. The converted wave reflection coefficient is a function of a density contrast at the subsurface interface and a shear velocity contrast at the subsurface interface. The method may further include determining a P wave incident angle such that the converted wave reflection coefficient is a function of substantially only the density contrast at the P wave incident angle. The P wave incident angle is referred to herein as θ. The method may further include calculating the density contrast based on the converted wave reflection coefficient at θ.

25 Claims, 7 Drawing Sheets

DETERMINING DENSITY CONTRAST AT SUBSURFACE INTERFACE

BACKGROUND

1. Field of the Invention

Implementations of various technologies described herein generally relate to density contrast determination at the subsurface interface.

2. Description of the Related Art

The following descriptions and examples do not constitute an admission as prior art by virtue of their inclusion within this section.

It is common knowledge in oil and gas industry that density is the key element in distinguishing commercial gas from fizz. Acoustic impedance may be successfully determined from PP inversion; however, that is not the case with density.

Some efforts have been made in using multicomponent seismic data to obtain density information. In particular, PP/PS joint inversion and PS inversion have been used to obtain density information from multicomponent seismic data. However, these processes have not been too successful due to technical difficulties involving PP/PS event registration, relative noisy gather of PS seismic data and the like.

SUMMARY

Described herein are implementations of various techniques for a method for subsurface exploration. In one implementation, the method may include receiving a gamma value at a subsurface interface, wherein the gamma value is a ratio of Vp/Vs at the subsurface interface. Vp is the average P wave velocity and Vs is the average S wave velocity. The method may further include receiving a converted wave reflection coefficient at the subsurface interface. The converted wave reflection coefficient is a function of a density contrast at the subsurface interface and a shear velocity contrast at the subsurface interface. The method may further include determining a P wave incident angle such that the converted wave reflection coefficient is a function of substantially only the density contrast at the P wave incident angle. The P wave incident angle is referred to herein as $\theta$. The method may further include calculating the density contrast based on the converted wave reflection coefficient at $\theta$.

Described herein are also implementations of various techniques for a computer-readable medium having stored thereon computer-executable instructions which, when executed by a computer, cause the computer to: receive a gamma value at a subsurface interface; receive a converted wave reflection coefficient at the subsurface interface based on the gamma value, wherein the converted wave reflection coefficient is a function of the density contrast and a shear velocity contrast; determine a P wave incident angle at which the contribution of the density contrast to the converted wave reflection coefficient is substantially greater than the contribution of the shear velocity contrast to the converted wave reflection coefficient, the P wave incident angle being referred to herein as $\theta_{S0}$; and calculate the density contrast based on $\theta_{S0}$, the gamma value and the converted wave reflection coefficient.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

Figure 1A:
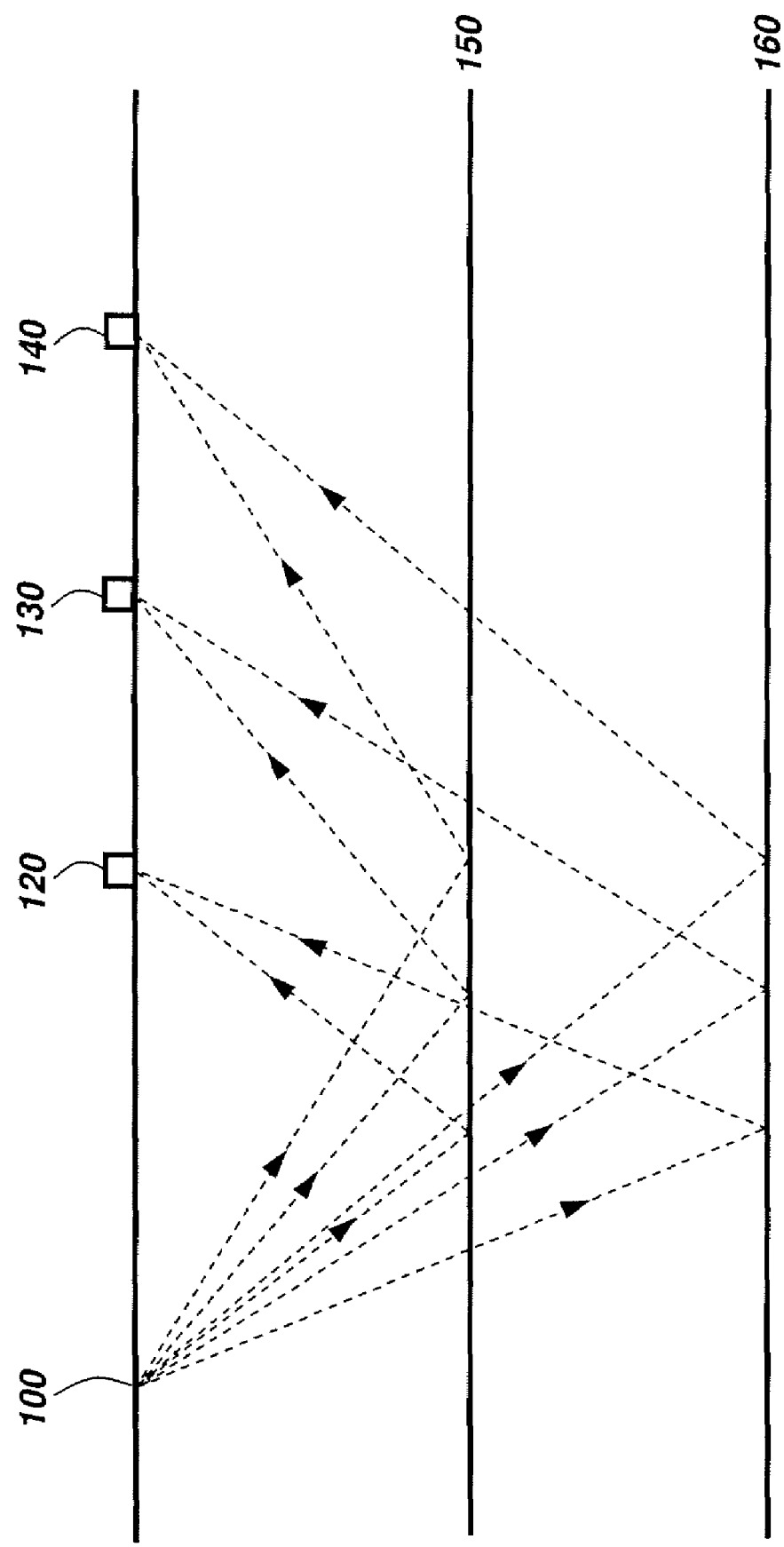
FIG. 1A illustrates a schematic diagram of a seismic survey that may be used in connection with implementations of various techniques described herein.

FIG. 1A illustrates a schematic diagram of a seismic survey that may be used in connection with implementations of various techniques described herein. A seismic survey is generally performed using at least one seismic source 100 and an array of seismic receivers 120, 130 and 140. For land seismic surveying, the seismic source 100 may be buried beneath the earth's surface and the seismic receivers 120, 130 and 140 may be disposed on the earth's surface. For marine seismic surveying, the seismic source 100 may be disposed below the sea water level and the seismic receivers 120, 130 and 140 may be disposed on the sea floor. When the source 100 is actuated, acoustic (or seismic) energy is emitted downwards into the earth and is reflected by geological interfaces that represent the change of rock elastic properties within the earth. The reflected energy may then be detected at the receivers 120, 130 and 140.

FIG. 1A also illustrates two geological structures 150 and 160 that act as reflectors of acoustic energy. These geological structures 150 and 160 may be formed by contrasting acoustic properties on both sides of the interfaces. As a result, the data acquired at each receiver 120, 130 and 140 may contain the responses from one "event" corresponding to a reflection of acoustic energy at the interface 150 and another "event" corresponding to a reflection of acoustic energy at the interface 160.

An event may be defined as the recorded signals that are associated with a seismic wave recorded by the receiver. These signals may be of short duration (tens of milliseconds) compared to the time taken for the seismic wave to travel from the source to the receiver (hundreds of milliseconds to several seconds). So, these signals may appear as distinct recordings on the seismic data trace. The time of the event would normally be the time of the onset of the signals.

Figure 1B:
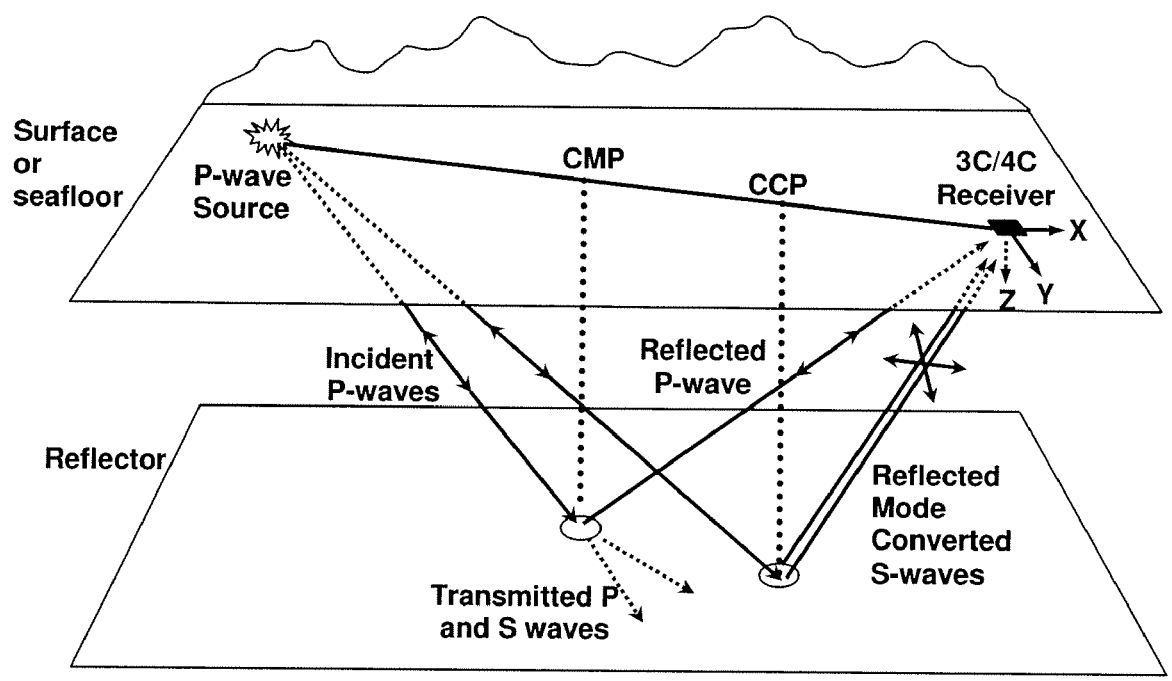
FIG. 1B illustrates a partial mode conversion to a shear wave.
Figure 1:
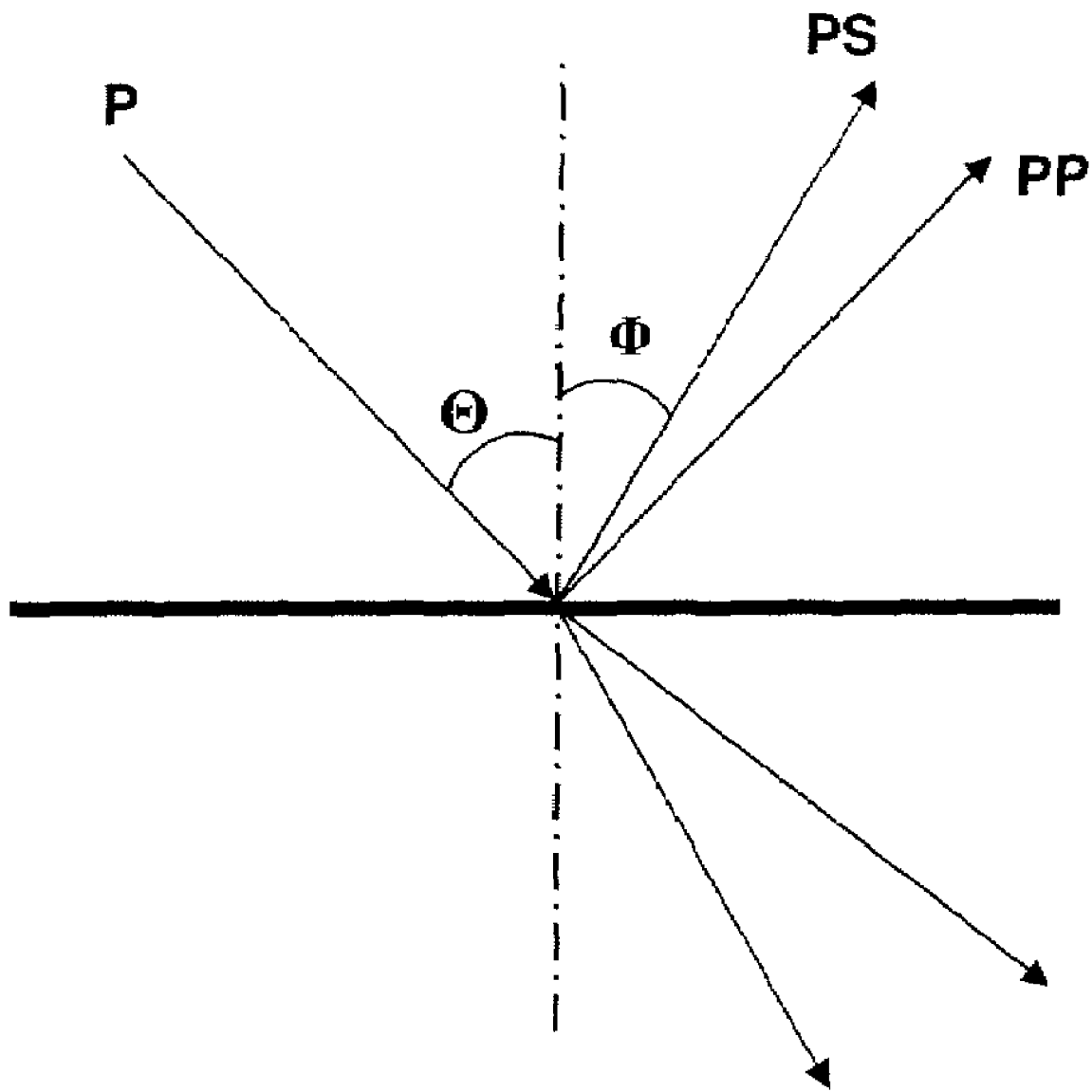
FIG. 1C illustrates Snell's law used in connection with various implementations described herein.

Acoustic energy emitted by the seismic source 100 may predominantly be a pressure-wave (or P-wave). When the acoustic energy undergoes reflection an interface 150, 160, it may also undergo a partial mode conversion to a shear wave (S-wave). The partial mode conversion to S wave is illustrated in FIG. 1B. As a result, the seismic wavefield acquired at the receivers 120, 130 and 140 may therefore contain both P-waves and S-waves.

Events arising from arrival of P-waves may be referred to as PP events, since they involve acoustic energy that is emitted as a P-wave and recorded on the receiver as a P-wave. Events arising from arrival of S-waves may be referred to as PS events, since they involve acoustic energy that is emitted as a P-wave but underwent a mode conversion to an S-wave upon reflection and is therefore recorded on the receiver as an S-wave. PP events occur more prominently in vertical components of the acquired seismic data, whereas PS events appear more prominently in the horizontal components of the acquired seismic data.

As mentioned above, implementations of various techniques described herein are directed to a method for obtaining the density contrast for a subsurface interface using PS events. The method may be based on the Aki and Richard equation, which is shown below:

$$R_{PS}(\theta) = \left(\frac{V_P \tan\phi}{2V_S}\right)\left[4\left(\frac{V_s}{V_P}\right)^2 \sin^2\theta - 4\frac{V_S}{V_P}\cos\theta\cos\phi\right]\frac{\Delta V_S}{V_S} - \left(\frac{V_P \tan\phi}{2V_S}\right)\left[1 - 2\left(\frac{V_s}{V_P}\right)^2 \sin^2\theta + 2\left(\frac{V_S}{V_P}\cos\theta\cos\phi\right)\right]\frac{\Delta\rho}{\rho}$$

Equation (1)

where $R_{PS}$ represents the converted wave (PS) reflection coefficient, $\theta$ represents the P wave incident angle at the subsurface interface, $V_P$ represents the average P wave velocity, $V_S$ represents the average S wave velocity, $\phi$ represents the S wave reflection angle, $\rho$ represents the average density and $$\frac{\Delta\rho}{\rho}$$

represent the density contrast. In one implementation, $\theta$ and $\phi$ are real numbers and less than 90 degrees. Assumptions for Equation (1) include a plan wave and that variation of physical parameters, e.g., $V_P$, $V_S$ and density, at the subsurface interface is small. Angles $\theta$ and $\phi$ are based on Snell's law, depicted in FIG. 1C.

Let $$\gamma = \frac{V_P}{V_s}.$$

Thus,

-continued $$\sin\phi = \frac{1}{\gamma}\sin\theta,$$

$$\cos\phi = \frac{1}{\gamma}\sqrt{\gamma^2 - \sin^2\theta},$$

and $$\tan\phi = \frac{\sin\theta}{\sqrt{\gamma^2 - \sin^2\theta}}.$$

Equation (1) may then be rewritten as:

$$R_{PS}(\theta, \gamma) = \frac{\sin\theta}{\gamma\sqrt{\gamma^2 - \sin^2\theta}}\left[2\sin^2\theta - 2\cos\theta\sqrt{\gamma^2 - \sin^2\theta}\right]\frac{\Delta V_S}{V_S} - \frac{\sin\theta}{\gamma\sqrt{\gamma^2 - \sin^2\theta}}\left[\sin^2\theta - \frac{1}{2}\gamma^2 - \cos\theta\sqrt{\gamma^2 - \sin^2\theta}\right]\frac{\Delta\rho}{\rho}.$$

Equation (2)

Equation (2) may be abbreviated as $$R_{PS}(\theta, \gamma) = S(\theta, \gamma)\frac{\Delta V_S}{V_S} + D(\theta, \gamma)\frac{\Delta\rho}{\rho},$$

Equation (3)

where $$S(\theta, \gamma) = \frac{\sin\theta}{\gamma\sqrt{\gamma^2 - \sin^2\theta}}\left[2\sin\theta - 2\cos\theta\sqrt{\gamma^2 - \sin^2\theta}\right]$$

and $$D(\theta, \gamma) = \frac{\sin\theta}{\gamma\sqrt{\gamma^2 - \sin^2\theta}}\left[\sin\theta - \frac{1}{2}\gamma^2 - \cos\theta\sqrt{\gamma^2 - \sin^2\theta}\right].$$

Once the Aki-Richard equation as in equation (1) is rewritten in the format of equation (3), the converted wave (PS) reflection coefficient $R_{PS}$ becomes a function of P wave incident angle $\theta$ and $\gamma$, which is the Vp/Vs ratio.

The coefficient of the shear velocity contrast, $S(\theta,\gamma)$, which may also be referred to as S term, may reach zero under the following two conditions:

(a) $\theta = 0$; or (b) $\theta = \arccos\sqrt{\frac{1}{\gamma^2 + 1}}$

Under the first condition, i.e., condition (a), the coefficient of the density contrast, $D(\theta,\gamma)$, which may also be referred to as D term, may also reach zero. However, under the second condition, i.e., condition (b), the D term does not reach zero. In fact, the D term almost reaches a maximum value. Thus, when $$\theta = \arccos\sqrt{\frac{1}{\gamma^2 + 1}},$$

the S term reaches zero while the D term is equal to:

$$D(\theta_{S0}, \gamma) = -\frac{\gamma \sin\theta_{S0}}{2\sqrt{\gamma^2 - \sin^2\theta_{S0}}} = -\frac{1}{2}, \quad \text{Equation (4)}$$

where $$\theta_{S0} = \arccos\sqrt{\frac{1}{\gamma^2 + 1}}.$$

Thus, when the S term reaches zero while the D term is equal −0.5, θ may be referred to as $\theta_{S0}$.

Further, when $$\theta = \arccos\sqrt{\frac{1}{\gamma^2 + 1}},$$

Equation (3) may be rewritten as $$R_{PS}(\theta_{S0}, \gamma) = D(\theta_{S0}, \gamma)\frac{\Delta\rho}{\rho} = -0.5\frac{\Delta\rho}{\rho}, \quad \text{Equation (5)}$$

where $D(\theta_{S0}, \gamma)$ is a constant (−0.5) for any given γ at $\theta_{S0}$.

$$\text{As such, } \frac{\Delta\rho}{\rho} = -2(R_{PS}(\theta_{S0}, \gamma)). \quad \text{Equation (5a)}$$

The density contrast is the same as the converted wave (PS) reflection coefficient $R_{PS}$ at $\theta_{S0}$ multiplied by a factor of −2.

Figure 2:
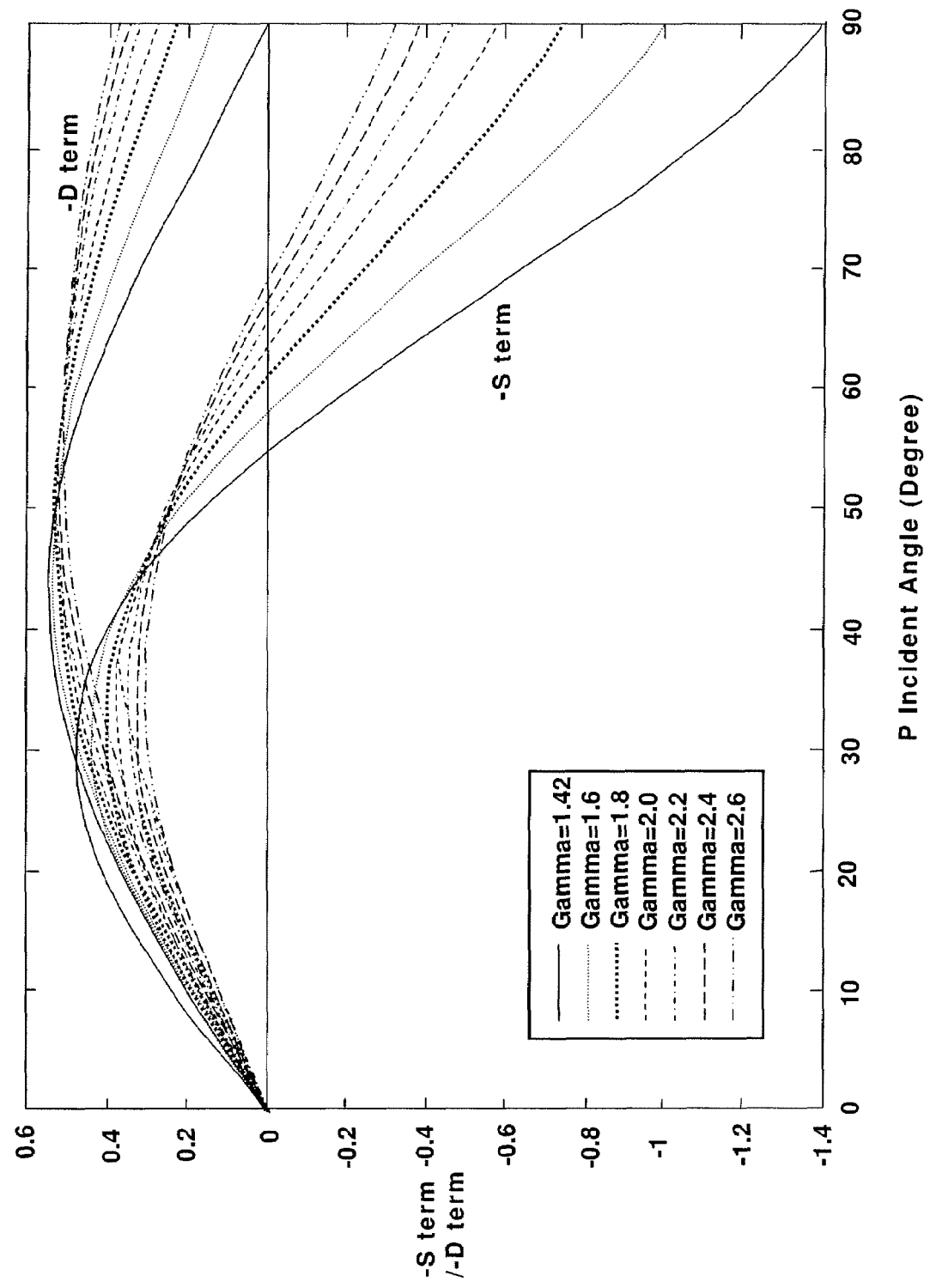
FIG. 2 illustrates a graph of $\theta$ versus S term and D term for a range of gamma values at subsurface interfaces in accordance with implementations of various techniques described herein.

FIG. 2 illustrates a graph of θ versus the magnitude of −S term and −D term for a range of gamma values at subsurface interfaces in the Gulf of Mexico. Notably, $\theta_{S0}$ is in the range of about 57 degrees to about 70 degrees for different gamma values, when the S term is zero while the D term reaches −0.5.

Figure 3:
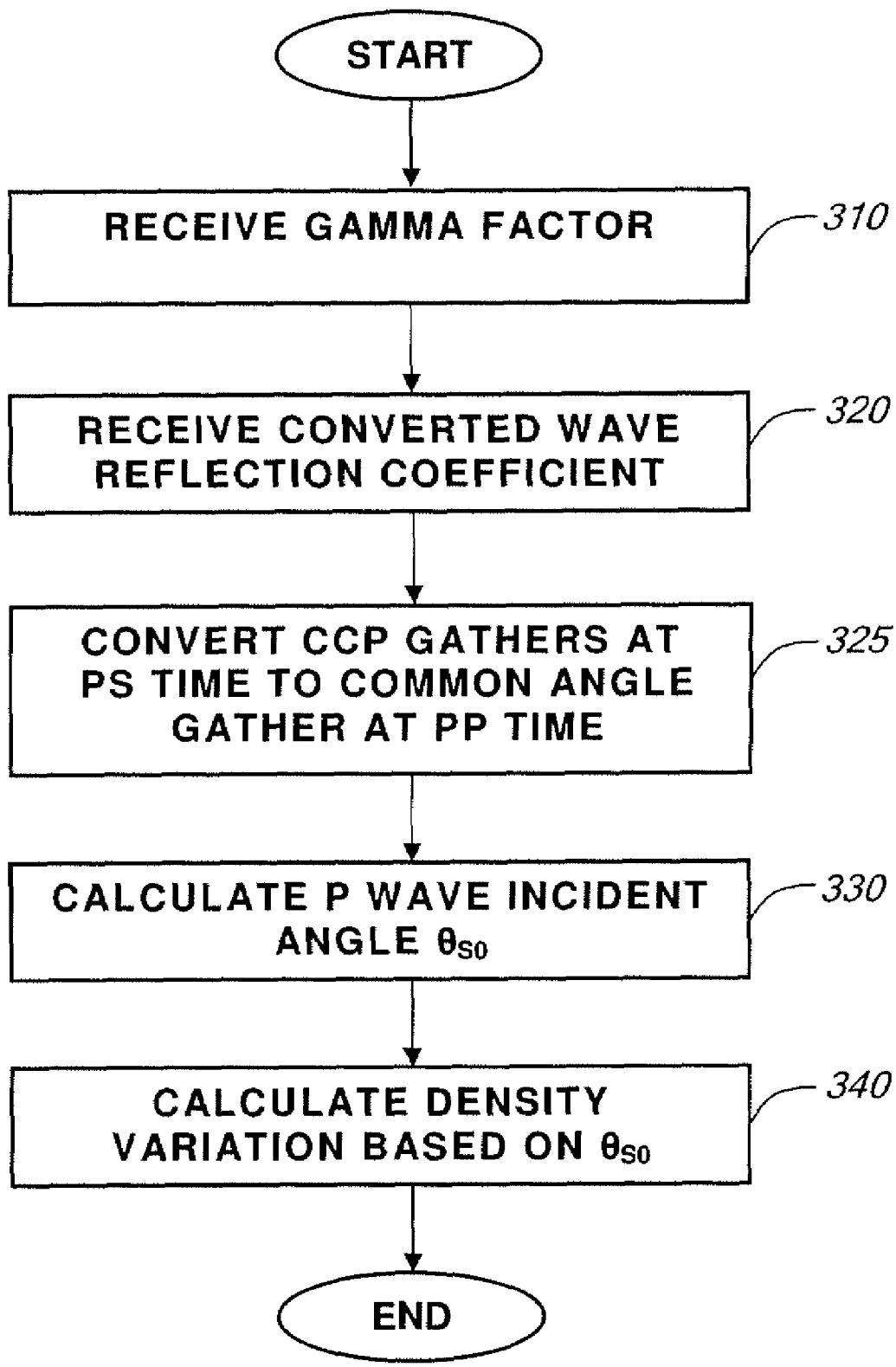
FIG. 3 illustrates a method for obtaining a density contrast of a subsurface interface in accordance with implementations of various techniques described herein.

FIG. 3 illustrates a method 300 for obtaining a density contrast at a subsurface interface in accordance with implementations of various techniques described herein. At step 310, a gamma value, γ, at the subsurface interface may be received. In one implementation, the gamma value may be obtained from seismic data processing, log data, regional rock physics study, vertical seismic profile (VSP), PP/PS event registration and the like.

At step 320, the converted wave (PS) reflection coefficient, $R_{PS}$, for the subsurface interface may be received. The reflection coefficient, $R_{PS}$, is at the same subsurface interface at which the gamma value is received at step 310. The reflection coefficient, $R_{PS}$, may be defined as the ratio of amplitude of the reflected S wave to the incident P wave. In one implementation, the converted wave reflection coefficient, $R_{PS}$, may be determined from multicomponent seismic data.

At step 325, common convert point gathers (CCP) at PS time, which is a set of offset traces, is converted to a common angle gather at PP time, which is a set of incident angle traces. The common angle gather traces may then be used in further processing.

At step 330, the P wave incident angle $\theta_{S0}$ may be calculated. In one implementation, $\theta_{S0}$ may be defined as the P wave incident angle that would cause the S term in Equation (3) to reach zero and the D term in Equation (3) to reach −0.5. Thus, at $\theta_{S0}$, the converted wave reflection coefficient is a function of only the density contrast at $\theta_{S0}$. In this manner, the shear velocity contrast may be decoupled from the density contrast. As discussed above, $\theta_{S0}$ may be calculated analytically using $$\theta_{S0} = \arccos\sqrt{\frac{1}{\gamma^2 + 1}},$$

where γ is the gamma value received in step 310.

At step 340, the density contrast, $$\frac{\Delta\rho}{\rho},$$

may be determined based on the gamma value and $\theta_{S0}$. In one implementation, the density contrast may be determined using Equation (5) or Equation (5a).

In another implementation, $\theta_{S0}$ may be determined numerically where S term is approaching zero. In many situations, as long as the S term contribution to $R_{PS}$ is sufficiently smaller compare to the D term contribution, then the S term may be safely ignored. In those situations, S does not need to be exactly zero. In such situations, where the S term is small, many θ's may be used, i.e., the $R_{PS}(\theta)$ may be used to calculate $$\frac{\Delta\rho}{\rho},$$

instead of the single $R_{PS}(\theta_{S0})$, which may not be available or that the data may not be desirable, e.g., due to noise considerations.

Once the density contrast at one interface is determined, density contrasts at other interfaces may be determined using a similar method. Thus, the densities of all layers of the subsurface may be determined by adding lower frequency information, e.g., using known density logs.

In another implementation, a single trace at $\theta_{S0}$ may not be sufficient due to noise. As such, stacking of selective traces at θ's near $\theta_{S0}$ may be performed in addition to calculating the P wave incident angle $\theta_{S0}$ at step 330.

Tables 1-3 list typical S-term and D-term values for θ's near $\theta_{S0}$ for various gamma values:

TABLE 1

| | | S term variation around $\theta_{s0}$ | | | |
|---|---|---|---|---|---|
| γ | $\theta_{s0}$ | $S(\theta_{s0} - 4, \gamma)$ | $S(\theta_{s0} + 4, \gamma)$ | $S(\theta_{s0} - 8, \gamma)$ | $S(\theta_{s0} + 8, \gamma)$ |
| 1.60 | 57.995 | −0.1151 | 0.1265 | −0.2156 | 0.2609 |
| 1.80 | 60.945 | −0.0973 | 0.1048 | −0.1843 | 0.2142 |
| 2.00 | 63.435 | −0.0842 | 0.0895 | −0.1608 | 0.1819 |
| 2.20 | 65.556 | −0.0743 | 0.0782 | −0.1426 | 0.1583 |
| 2.40 | 67.380 | −0.0665 | 0.0694 | −0.1282 | 0.1402 |
| 2.60 | 68.962 | −0.0602 | 0.0626 | −0.1165 | 0.1260 |

TABLE 2

D term variation around $\theta_{s0}$

| γ | $\theta_{s0}$ | $D(\theta_{s0}, \gamma)$ | $D(\theta_{s0}-4, \gamma)$ | $D(\theta_{s0}+4, \gamma)$ | $D(\theta_{s0}-8, \gamma)$ | $D(\theta_{s0}+8, \gamma)$ |
|---|---|---|---|---|---|---|
| 1.60 | 57.995 | −0.5000 | −0.5263 | −0.4661 | −0.5440 | −0.4259 |
| 1.80 | 60.945 | −0.5000 | −0.5222 | −0.4718 | −0.5373 | −0.4386 |
| 2.00 | 63.435 | −0.5000 | −0.5191 | −0.4758 | −0.5322 | −0.4473 |
| 2.20 | 65.556 | −0.5000 | −0.5168 | −0.4787 | −0.5282 | −0.4537 |
| 2.40 | 67.380 | −0.5000 | −0.5149 | −0.4810 | −0.5250 | −0.4586 |
| 2.60 | 68.962 | −0.5000 | −0.5134 | −0.4828 | −0.5224 | −0.4624 |

TABLE 3

S-term, with $\Delta\theta_2$

| γ | $\theta_{s0}$ | $S(\theta_{s0}-4, \gamma)$ | $\Delta\theta_2$/S-term | $S(\theta_{s0}-8, \gamma)$ | $\Delta\theta_2$/S-term |
|---|---|---|---|---|---|
| 1.60 | 57.995 | −0.1151 | 3.6495<br>0.1151 | −0.2156 | 6.6708<br>0.2156 |
| 1.80 | 60.945 | −0.0973 | 3.7187<br>0.0973 | −0.1843 | 6.9156<br>0.1843 |
| 2.00 | 63.435 | −0.0842 | 3.7670<br>0.0842 | −0.1608 | 7.0915<br>0.1608 |
| 2.20 | 65.556 | −0.0743 | 3.8022<br>0.0743 | −0.1426 | 7.2220<br>0.1426 |
| 2.40 | 67.380 | −0.0665 | 3.8286<br>0.0665 | −0.1282 | 7.3214<br>0.1282 |
| 2.60 | 68.962 | −0.0602 | 3.8490<br>0.0602 | −0.1165 | 7.3992<br>0.1165 |

Figure 4:
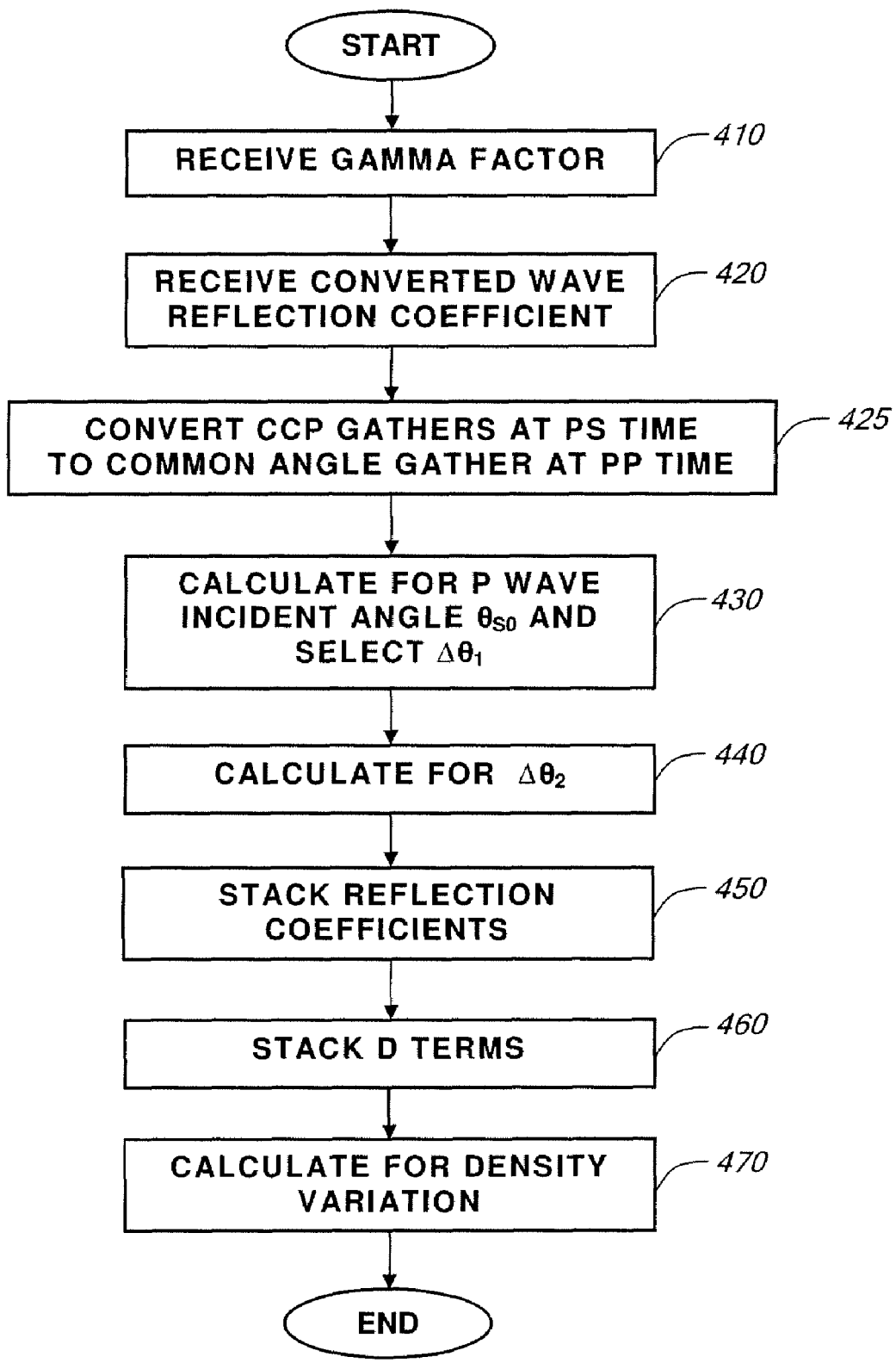
FIG. 4 illustrates a method for obtaining a density contrast at a subsurface interface by stacking of selective traces at $\theta$'s near $\theta_{S0}$ in accordance with implementations of various techniques described herein.

FIG. 4 illustrates a method 400 for obtaining a density contrast at a subsurface interface by stacking of selective traces at θ's near $\theta_{SO}$ in accordance with implementations of various techniques described herein. At step 410, a gamma value, γ, at the subsurface interface may be received. At step 420, a converted wave (PS) reflection coefficient, $R_{PS}$, at the subsurface interface may be received. At step 425, common convert point gathers (CCP) at PS time, which is a set of offset traces, is converted to a common angle gather at PP time, which is a set of incident angle traces. The common angle gather traces may then be used in further processing. Steps 410-425 are described in more detail with reference to steps 310-325 in the above paragraphs.

At step 430, the P wave incident angle $\theta_{S0}$ may be calculated. The details of the calculation of $\theta_{S0}$ are provided with reference to step 330 above. In addition, $\Delta\theta_1$ may be selected, where $\Delta\theta_1$ is defined as a change in P wave incident angle near $\theta_{S0}$. $\Delta\theta_1$ may be any arbitrary angle differences, e.g., 4°, 8° or larger as in Tables 1-3.

At step 440, $\Delta\theta_2$ may be calculated, where $\Delta\theta_2$ is defined as a change in P wave incident angle near $\theta_{S0}$ such that $$S(\theta_{S0}+\Delta\theta_1,\gamma)=-S(\theta_{S0}-\Delta\theta_2,\gamma).$$

Notably, the S term reverses polarity at $\theta_{S0}$. The difference percentage of magnitude between $S(\theta_{S0}+\Delta\theta, \gamma)$ and $S(\theta_{S0}-\Delta\theta, \gamma)$ increases as γ decreases. As such, many $\Delta\theta_1$ and $\Delta\theta_2$ may be selected or determined, respectively, for a given γ. On the contrary, the D term does not reverse polarity at $\theta_{S0}$. The difference percentage of magnitude between $D(\theta_{S0}+\Delta\theta, \gamma)$ and $D(\theta_{S0}-\Delta\theta, \gamma)$ increases as γ decreases.

For example as shown in Tables 1-3, for γ at 1.6, $\theta_{S0}$ is 57.995°. Selecting an arbitrary $\Delta\theta_1$ as −4°, then $\Delta\theta_2$ is 3.6495°. Similarly, if the arbitrary $\Delta\theta_1$ is −8°, then $\Delta\theta_2$ is 6.6708°. $\Delta\theta_2$ can be determined numerically or analytically.

In one implementation, $\Delta\theta_2$ may be determined analytically according to:

$$\Delta\theta_2 = \frac{(\gamma^2+1) - \sqrt{(\gamma^2+1)^2 - (\gamma^2+1)(\gamma^2+3)S(\theta_{S0}+\Delta\theta_1)}}{(\gamma^2+1)(\gamma^2+3)/\gamma^3}.$$ Equation (6)

At step 450, the converted wave reflection coefficients for the trace at $\theta_{S0}$, $\theta_{S0}+\Delta\theta_1$ and $\theta_{S0}-\Delta\theta_2$ may be stacked, as follows $$R_{PS}(\theta_{S0}+\Delta\theta_1,\gamma)+R_{PS}(\theta_{S0},\gamma)+R_{PS}(\theta_{S0}-\Delta\theta_2,\gamma)$$ Equation (7).

At step 460, the D terms for the trace at $\theta_{S0}$, $\theta_{S0}+\Delta\theta_1$ and $\theta_{S0}-\Delta\theta_2$ may be stacked as follows:

$$D(\theta_{S0}+\Delta\theta_1,\gamma)+D(\theta_{S0},\gamma)+D(\theta_{S0}-\Delta\theta_2,\gamma)$$ Equation (8).

At step 470, the density contrast may be calculated based on the stacked converted wave reflection coefficients and stacked the D terms. In one implementation, the density contrast $$\frac{\Delta\rho}{\rho}.$$

may be calculated according to:

$$\frac{\Delta\rho}{\rho} = (R_{PS}(\theta_{S0}+\Delta\theta_1, \gamma) + R_{PS}(\theta_{S0}, \gamma) + R_{PS}(\theta_{S0}-\Delta\theta_2, \gamma))/$$
$$(D(\theta_{S0}+\Delta\theta_1, \gamma) + D(\theta_{S0}, \gamma) + D(\theta_{S0}-\Delta\theta_2, \gamma)).$$ Equation (9)

Although FIG. 4 is illustrated with reference to stacking three traces at θ's near $\theta_{SO}$, it should be understood that in some implementations more than three traces θ's near $\theta_{SO}$ may be stacked. The number of traces to be stacked may be determined based on the quality of the seismic data, accuracy of the resulting density value and many other considerations. For example, as shown in Tables 1-3, for gamma at 1.6, the five traces at incident angles of 57.995°, (57.995°−4°), (57.995°+3.6495°), (57.995°−8°), (57.995°+6.6708°) may be stacked.

In another implementation of stacking, $\Delta\theta_2$ may be selected to be the same as $\Delta\theta_1$. In this manner, the S-terms do not cancel entirely. As a result, the resulting density contrast $$\frac{\Delta\rho}{\rho}$$

may have some error. In general, for most gamma values, so long as $\Delta\theta_1$ is less than 10% of $\theta_{S0}$, the residue error due the S-term is small and negligible.

In yet another implementation of stacking, Equation 9 may be simplified approximately as:

$$\frac{\Delta\rho}{\rho} = -(R_{PS}(\theta_{S0}+\Delta\theta, \gamma) + R_{PS}(\theta_{S0}, \gamma) + R_{PS}(\theta_{S0}-\Delta\theta, \gamma))/1.5$$

where $\Delta\theta$ is less than 10% of $\theta_{S0}$, and the sum of three D terms is approximately −1.5.

Further, in some implementations, dynamic stacking, i.e., time variable, may also be used for whole time section, e.g., from shallow to deep, e.g., 1000 ms to 5000 ms. In PP time, when gamma changes with the depth of the subsurface interface, $\theta_{SO}$ may be changed accordingly.

In this manner, various techniques described herein may be used to determine a density contrast without using any inversion techniques. Various techniques described herein have proven to be effective even for relatively noisy data. As such, in one implementation, various techniques described herein may be used to calculate density contrasts for a plurality of subsurface interfaces. The density contrasts may then be used to calculate densities at the subsurface interfaces. The calculated densities may then be used to locate gas.

Figure 5:
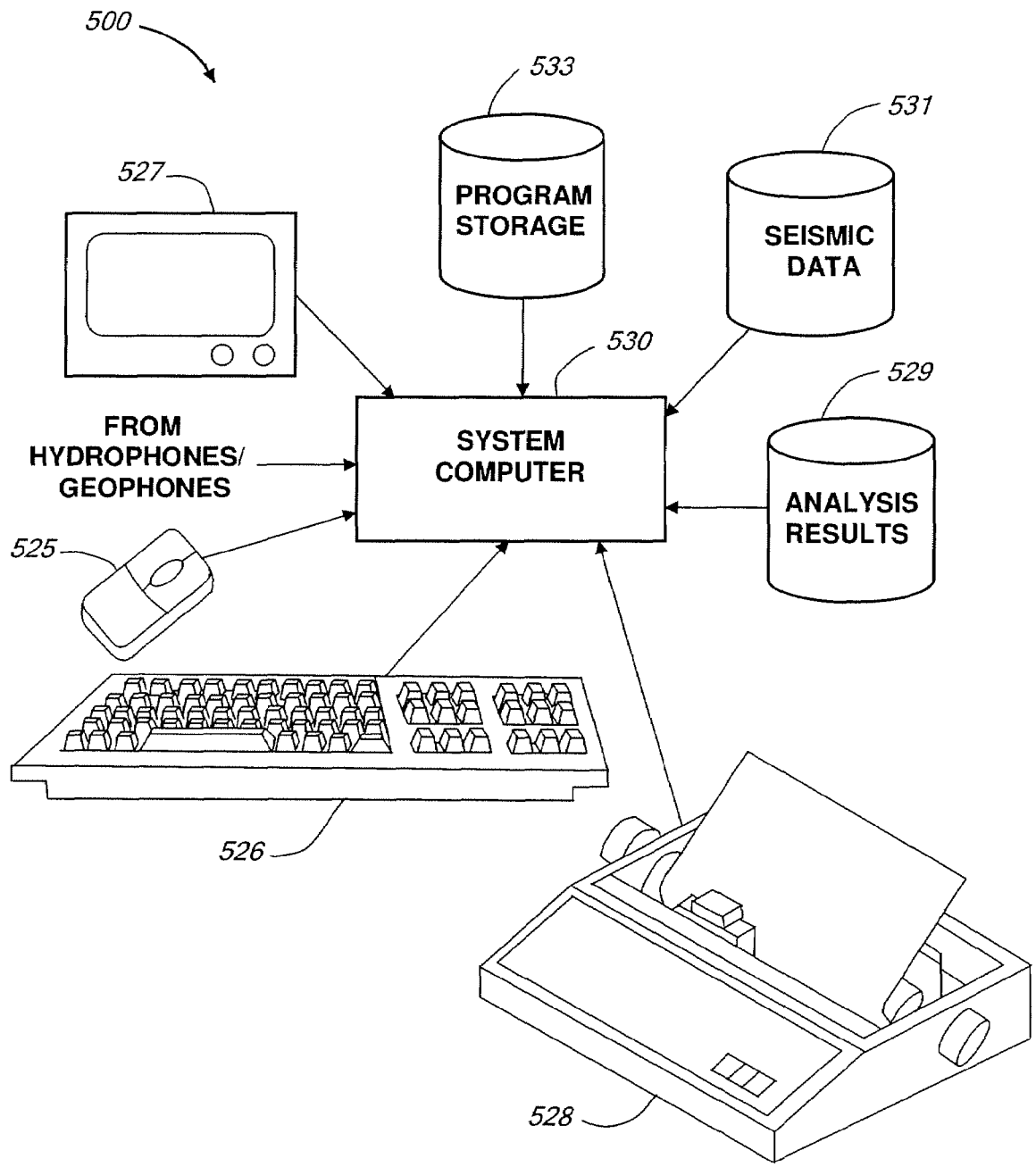
FIG. 5 illustrates a computing system, into which implementations of various technologies described herein may be implemented.

FIG. 5 illustrates a computing system 500, into which implementations of various technologies described herein may be implemented. The computing system 500 may include one or more system computers 530, which may be implemented as any conventional personal computer or server. However, those skilled in the art will appreciate that implementations of various technologies described herein may be practiced in other computer system configurations, including hypertext transfer protocol (HTTP) servers, hand-held devices, multiprocessor systems, microprocessor-based or programmable consumer electronics, network PCs, mini-computers, mainframe computers, and the like.

The system computer 530 may be in communication with disk storage devices 529, 531, and 533, which may be external hard disk storage devices. It is contemplated that disk storage devices 529, 531, and 533 are conventional hard disk drives, and as such, will be implemented by way of a local area network or by remote access. Of course, while disk storage devices 529, 531, and 533 are illustrated as separate devices, a single disk storage device may be used to store any and all of the program instructions, measurement data, and results as desired.

In one implementation, seismic data from the receivers may be stored in disk storage device 531. The system computer 530 may retrieve the appropriate data from the disk storage device 531 to process seismic data according to program instructions that correspond to implementations of various technologies described herein. The program instructions may be written in a computer programming language, such as C++, Java and the like. The program instructions may be stored in a computer-readable medium, such as program disk storage device 533. Such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the system computer 530. Communication media may embody computer readable instructions, data structures, and program modules. By way of example, and not limitation, communication media may include wired media such as a wired network or direct-wired connection, and wireless media such as acoustic, RF, infrared and other wireless media. Combinations of any of the above may also be included within the scope of computer readable media.

In one implementation, the system computer 530 may present output primarily onto graphics display 527, or alternatively via printer 528. The system computer 530 may store the results of the methods described above on disk storage 529, for later use and further analysis. The keyboard 526 and the pointing device (e.g., a mouse, trackball, or the like) 525 may be provided with the system computer 530 to enable interactive operation.

The system computer 530 may be located at a data center remote from the survey region. The system computer 530 may be in communication with the receivers (either directly or via a recording unit, not shown), to receive signals indicative of the reflected seismic energy. These signals, after conventional formatting and other initial processing, may be stored by the system computer 530 as digital data in the disk storage 531 for subsequent retrieval and processing in the manner described above. While FIG. 5 illustrates the disk storage 531 as directly connected to the system computer 530, it is also contemplated that the disk storage device 531 may be accessible through a local area network or by remote access. Furthermore, while disk storage devices 529, 531 are illustrated as separate devices for storing input seismic data and analysis results, the disk storage devices 529, 531 may be implemented within a single disk drive (either together with or separately from program disk storage device 533), or in any other conventional manner as will be fully understood by one of skill in the art having reference to this specification.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for subsurface exploration, comprising:
   receiving seismic data that were acquired by one or more seismic sensors;
   receiving a gamma value at a subsurface interface, wherein the gamma value is a ratio of Vp/Vs at the subsurface interface, wherein Vp is the average P wave velocity and Vs is the average S wave velocity;
   receiving a converted wave reflection coefficient at the subsurface interface, wherein the converted wave reflection coefficient is a function of a density contrast at the subsurface interface and a shear velocity contrast at the subsurface interface, and the converted wave reflection coefficient is determined from the seismic data;
   determining a P wave incident angle such that the converted wave reflection coefficient is a function of substantially only the density contrast at the P wave incident angle, wherein the P wave incident angle is referred to herein as $\theta$; and
   calculating the density contrast based on the converted wave reflection coefficient at $\theta$.

2. The method of claim 1, wherein the density contrast is calculated according to $$\frac{\Delta\rho}{\rho} = -2(R_{PS}(\theta_{S0}, \gamma)),$$

where $$\frac{\Delta\rho}{\rho}$$

represents the density contrast, $\gamma$ represents the gamma value, and $R_{PS}(\theta_{S0},\gamma)$ represents the converted wave reflection coefficient as a function of $\theta_{S0}$ and the gamma value.

3. The method of claim 1, wherein a contribution of the shear velocity contrast to the converted wave reflection coefficient is zero and the P wave incident angle is referred to as $\theta_{S0}$.

4. The method of claim 3, wherein the converted wave reflection coefficient is expressed as $$R_{PS}(\theta, \gamma) = S(\theta, \gamma)\frac{\Delta V_S}{V_S} + D(\theta, \gamma)\frac{\Delta\rho}{\rho},$$

where $S(\theta,\gamma)$ represents a coefficient of the shear velocity contrast at the subsurface interface and $D(\theta,\gamma)$ represents a coefficient of the density contrast at the subsurface interface; the coefficient of the shear velocity contrast is expressed as $$S(\theta, \gamma) = \frac{\sin\theta}{\gamma\sqrt{\gamma^2 - \sin^2\theta}}\left[2\sin^2\theta - 2\cos\theta\sqrt{\gamma^2 - \sin^2\theta}\right],$$

where $\theta$ represents a P wave incident angle and $\gamma$ represents the gamma value; and
the coefficient of the density contrast is expressed as $$D(\theta, \gamma) = \frac{\sin\theta}{\gamma\sqrt{\gamma^2 - \sin^2\theta}}\left[\sin^2\theta - \frac{1}{2}\gamma^2 - \cos\theta\sqrt{\gamma^2 - \sin^2\theta}\right].$$

5. The method of claim 4, wherein calculating the density contrast comprises calculating the coefficient of the density contrast as a function of $\theta_{S0}$ and the gamma value.

6. The method of claim 3, wherein $\theta_{S0}$ is determined according to $$\theta_{S0} = \arccos\sqrt{\frac{1}{\gamma^2 + 1}},$$

where $\gamma$ represents the gamma value.

7. The method of claim 3, further comprising:
selecting a plurality of first change $\Delta\theta_1$ in P wave incident angle;
determining a plurality of corresponding $\Delta\theta_2$ in P wave incident angle such that $S(\theta_{S0}+\Delta\theta_1, \gamma)=-S(\theta_{S0}-\Delta\theta_2, \gamma)$, where S represents the coefficient of the shear velocity contrast, and $\gamma$ represents the gamma value;
stacking a first converted wave reflection coefficient as a function of $\theta_{S0}$ and the gamma value, a second converted wave reflection coefficient as a function of $\theta_{S0}+\Delta\theta_1$ and the gamma value, and a third converted wave reflection coefficient as a function of $\theta_{S0}-\Delta\theta_2$ and the gamma value; and
stacking a first coefficient of the density contrast as a function of $\theta_{S0}$ and the gamma value, a second coefficient of the density contrast as a function of $\theta_{S0}+\Delta\theta_1$ and the gamma value, and a third coefficient of the density contrast as a function of $\theta_{S0}-\Delta\theta_2$ and the gamma value.

8. The method of claim 3, further comprising:
selecting a first change $\Delta\theta_1$ in P wave incident angle near $\theta_{S0}$;
stacking a first converted wave reflection coefficient as a function of $\theta_{S0}$, a second converted wave reflection coefficient as a function of $\theta_{S0}+\Delta\theta_1$ and a third converted wave reflection coefficient as a function of $\theta_{S0}-\Delta\theta_2$.

9. The method of claim 8, wherein the first change $\Delta\theta_1$ is within ten percent of $\theta_{S0}$.

10. The method of claim 8, further comprising:
stacking a first coefficient of the density contrast as a function of $\theta_{S0}$, a second coefficient of the density contrast as a function of $\theta_{S0}+\Delta\theta_1$, and a third coefficient of the density contrast as a function of $\theta_{S0}-\Delta\theta_1$.

11. The method of claim 3, further comprising:
selecting a first change $\Delta\theta_1$ in P wave incident angle;
determining a second change $\Delta\theta_2$ in P wave incident angle such that $S(\theta_{S0}+\Delta\theta_1, \gamma)=-S(\theta_{S0}-\Delta\theta_2, \gamma)$, where S represents the coefficient of the shear velocity contrast and $\gamma$ represents the gamma value;
stacking a first converted wave reflection coefficient as a function of $\theta_{S0}$ and the gamma value, a second converted wave reflection coefficient as a function of $\theta_{S0}+\Delta\theta_1$ and the gamma value, and a third converted wave reflection coefficient as a function of $\theta_{S0}-\Delta\theta_2$ and the gamma value; and
stacking a first coefficient of the density contrast as a function of $\theta_{S0}$ and the gamma value, a second coefficient of the density contrast as a function of $\theta_{S0}+\Delta\theta_1$ and the gamma value, and a third coefficient of the density contrast as a function of $\theta_{S0}-\Delta\theta_2$ and the gamma value.

12. The method of claim 11, wherein the density contrast is calculated based on the stacked converted wave reflection coefficient and the stacked coefficient of the density contrast.

13. The method of claim 11, wherein the density contrast is calculated according to: $$\frac{\Delta\rho}{\rho} = (R_{PS}(\theta_{S0} + \Delta\theta_1, \gamma) + R_{PS}(\theta_{S0}, \gamma) + R_{PS}(\theta_{S0} - \Delta\theta_2, \gamma))/$$
$$(D(\theta_{S0} + \Delta\theta_1, \gamma) + D(\theta_{S0}, \gamma) + D(\theta_{S0} - \Delta\theta_2, \gamma)),$$

where $R_{PS}(\theta_{S0},\gamma)$ represents the first converted wave reflection coefficient, $R_{PS}(\theta_{S0}+\Delta\theta_1, \gamma)$ represents the second converted wave reflection coefficient, $R_{PS}(\theta_{S0}-\Delta\theta_2,\gamma)$ represents the third converted wave reflection coefficient, $D(\theta_{S0},\gamma)$ represents the first coefficient of the density contrast, $D(\theta_{S0}+\Delta\theta_1, \gamma)$ represents the second coefficient of the density contrast, and $D(\theta_{S0}-\Delta\theta_2, \gamma)$ represents the third coefficient of the density contrast.

14. The method of claim 11, wherein the density at one side of the interface is determined using the density contrast at the interface and the density of the other side of the interface.

15. The method of claim 14, wherein the densities at all subsurface layers are determined from the density contrasts.

16. The method of claim 11, wherein the density contrast is used to explore gas in a subsurface.

17. A computer storage medium having stored thereon computer-executable instructions which, when executed by a computer, cause the computer to:
- receive a gamma value at a subsurface interface;
- receive a converted wave reflection coefficient at the subsurface interface based on the gamma value, wherein the converted wave reflection coefficient is a function of the density contrast and a shear velocity contrast, and the converted wave reflection coefficient is determined from seismic data;
- determine a P wave incident angle at which the contribution of the density contrast to the converted wave reflection coefficient is substantially greater than the contribution of the shear velocity contrast to the converted wave reflection coefficient, the P wave incident angle being referred to herein as $\theta_{S0}$; and
- calculate the density contrast based on $\theta_{S0}$, the gamma value and the converted wave reflection coefficient.

18. The computer storage medium of claim 17, wherein the contribution of the shear velocity contrast to the converted wave reflection coefficient is zero.

19. The computer storage medium of claim 17, wherein the converted wave reflection coefficient is expressed as $$R_{PS}(\theta, \gamma) = S(\theta, \gamma)\frac{\Delta V_S}{V_S} + D(\theta, \gamma)\frac{\Delta \rho}{\rho},$$

where $$\frac{\Delta V_S}{V_S}$$

represents the shear velocity contrast at the subsurface interface, $$\frac{\Delta \rho}{\rho}$$

represents the density contrast at the subsurface interface, $S(\theta,\gamma)$ represents a coefficient of the shear velocity contrast and $D(\theta,\gamma)$ represents a coefficient of the density contrast.

20. The computer storage medium of claim 17, wherein the coefficient of the shear velocity contrast is zero while the coefficient of the density contrast reaches a maximum value at $\theta_{S0}$.

21. The computer storage medium of claim 17, further comprising computer-executable instructions which, when executed by a computer, cause the computer to:
- select a first change in P wave incident angle near $\theta_{S0}$;
- determine a second change in P wave incident angle near $\theta_{S0}$ such that $S(\theta_{S0}+\Delta\theta_1, \gamma)=-S(\theta_{S0}-\Delta\theta_2, \gamma)$, where S represents the coefficient of the shear velocity contrast, $\Delta\theta_1$ represents the first change, $\Delta\theta_2$ represents the second change and $\gamma$ represents the gamma value;
- stack a first converted wave reflection coefficient as a function of $\theta_{S0}$ and the gamma value, a second converted wave reflection coefficient as a function of $\theta_{S0}+\Delta\theta_1$ and the gamma value, and a third converted wave reflection coefficient as a function of $\theta_{S0}-\Delta\theta_2$ and the gamma value; and
- stack a first coefficient of the density contrast as a function of $\theta_{S0}$ and the gamma value, a second coefficient of the density contrast as a function of $\theta_{S0}+\Delta\theta_1$ and the gamma value, and a third coefficient of the density contrast as a function of $\theta_{S0}-\Delta\theta_2$ and the gamma value.

22. The computer storage medium of claim 21, wherein the density contrast is calculated according to:

$$\frac{\Delta\rho}{\rho} = (R_{PS}(\theta_{S0} + \Delta\theta_1, \gamma) + R_{PS}(\theta_{S0}, \gamma) + R_{PS}(\theta_{S0} - \Delta\theta_2, \gamma))/$$
$$(D(\theta_{S0} + \Delta\theta_1, \gamma) + D(\theta_{S0}, \gamma) + D(\theta_{S0} - \Delta\theta_2, \gamma)),$$

where $R_{PS}(\theta_{S0},\gamma)$ represents the first converted wave reflection coefficient, $R_{PS}(\theta_{S0}+\Delta\theta_1, \gamma)$ represents the second converted wave reflection coefficient, $R_{PS}(\theta_{S0}-\Delta\theta_2,\gamma)$ represents the third converted wave reflection coefficient, $D(\theta_{S0},\gamma)$ represents the first coefficient of the density contrast, $D(\theta_{S0}+\Delta\theta_1, \gamma)$ represents the second coefficient of the density contrast, and $D(\theta_{S0}-\Delta\theta_2, \gamma)$ represents the third coefficient of the density contrast.

23. A computer system, comprising:
- a processor; and
- a memory comprising program instructions executable by the processor to:
  - receive a gamma value at the subsurface interface;
  - receive a converted wave reflection coefficient at the subsurface interface based on the gamma value, wherein the converted wave reflection coefficient is a function of the density contrast and a shear velocity contrast, and the converted wave reflection coefficient is determined from seismic data;
  - determine a P wave incident angle such that the converted wave reflection coefficient is a function of substantially only the density contrast at the P wave incident angle, the P wave incident angle being referred to herein as $\theta_{S0}$; and
  - calculate the density contrast based on $\theta_{S0}$, the gamma value and the converted wave reflection coefficient.

24. The computer system of claim 23, wherein $\theta_{S0}$ is determined according to $$\theta_{S0} = \arccos\sqrt{\frac{1}{\gamma^2+1}},$$

where $\gamma$ represents the gamma value.

25. The computer system of claim 23, wherein the density contrast is calculated according to $$R_{PS}(\theta_{S0}, \gamma) = D(\theta_{S0}, \gamma)\frac{\Delta\rho}{\rho},$$

where $$\frac{\Delta\rho}{\rho}$$

represents the density contrast, $\gamma$ represents the gamma value, $D(\theta_{S0},\gamma)$ represents a coefficient of the density contrast as a function of $\theta_{S0}$ and the gamma value and $R_{PS}(\theta_{S0}\gamma)$ represents the converted wave reflection coefficient as a function of $\theta_{S0}$ and the gamma value.

* * * * *